US012590954B2

(12) United States Patent
Wei et al.

(10) Patent No.: US 12,590,954 B2
(45) Date of Patent: Mar. 31, 2026

(54) NEURAL STEM CELL-INDUCED DIFFERENTIAL MEDIUM AND INDUCTION DIFFERENTIATION METHOD

(71) Applicant: IREGENE THERAPEUTICS, CO., LTD., Chengdu (CN)

(72) Inventors: Jun Wei, Wuhan (CN); Meng Cai, Wuhan (CN); Lumeng Niu, Wuhan (CN); Jia Zhou, Wuhan (CN); Mengying Hou, Wuhan (CN)

(73) Assignee: IREGENE THERAPEUTICS, CO., LTD., Chengdu (CN)

( * ) Notice: Subject to any disclaimer, the term of this patent is extended or adjusted under 35 U.S.C. 154(b) by 371 days.

(21) Appl. No.: 18/269,001

(22) PCT Filed: Jan. 8, 2021

(86) PCT No.: PCT/CN2021/070893
§ 371 (c)(1),
(2) Date: Jun. 22, 2023

(87) PCT Pub. No.: WO2022/134229
PCT Pub. Date: Jun. 30, 2022

(65) Prior Publication Data
US 2024/0053327 A1    Feb. 15, 2024

(30) Foreign Application Priority Data

Dec. 23, 2020    (CN) .......................... 202011538099.2

(51) Int. Cl.
*G01N 33/50*        (2006.01)
*C12N 5/071*        (2010.01)
*C12N 5/079*        (2010.01)

(52) U.S. Cl.
CPC ....... *G01N 33/5082* (2013.01); *C12N 5/0618* (2013.01); *C12N 5/0697* (2013.01); *C12N 2500/25* (2013.01); *C12N 2500/32* (2013.01); *C12N 2501/15* (2013.01); *C12N 2501/155* (2013.01); *C12N 2513/00* (2013.01)

(58) Field of Classification Search
None
See application file for complete search history.

(56) References Cited

U.S. PATENT DOCUMENTS

| | | | | |
|---|---|---|---|---|
| 2015/0030570 A1* | 1/2015 | Pan | ...................... | C12N 5/0623 435/325 |
| 2019/0100724 A1* | 4/2019 | Sato | ..................... | C12N 5/0037 |
| 2019/0218514 A1 | 7/2019 | Kii et al. | | |

FOREIGN PATENT DOCUMENTS

| | | |
|---|---|---|
| CN | 1778902 A | 5/2006 |
| CN | 102604894 A | 7/2012 |
| CN | 108384755 A | 8/2018 |
| CN | 109072179 A | 12/2018 |
| CN | 109294991 A | 2/2019 |
| CN | 109628383 A | 4/2019 |
| CN | 109996870 A | 7/2019 |
| CN | 110753753 A | 2/2020 |
| CN | 110760476 A | 2/2020 |
| KR | 20170006949 A | 1/2017 |
| WO | 2012034101 A2 | 3/2012 |
| WO | WO2014176606 A1 | 10/2014 |
| WO | WO2017204340 A1 | 11/2017 |
| WO | WO2020045990 A | 3/2020 |
| WO | 2021232830 A1 | 11/2021 |
| WO | 2022134031 A1 | 6/2022 |

OTHER PUBLICATIONS

Lyu.Linjie, Generation of Selfrenewing Neural Stem Cells from Human Embryonic Stem Cells, *China Doctoral Dissertations and Master's Theses Full-text Database (Master)*. *Medicine and Health Sciences*, No. 04.Apr. 15, 2017 (Apr. 15, 2017), ISSN:1674-0246.
Jingli Cai et al., BMP and TGF-Bpathway mediators are critical upstream regulators of Wntsignaling during midbrain dopamine differentiation in human pluripotent stem cells, *Developmmental Biology*.vol. 376.Jan. 23, 2013 (Jan. 23, 2013), ISSN:1095-564X.
Chhibber Tanya et al:"CNS organoids: an innovative tool for neurological disease modeling and drug neurotoxicity screening", Drug Discovery Today , Elsevier , Amsterdam, NL, vol. 25 , No. 2, Nov. 26, 2019(Nov. 26, 2019) , pp. 456-465 , XP086060427 , ISSN: 1359-6446 , DOT:10.1016/J.DRUDIS.2019.11.010.

* cited by examiner

*Primary Examiner* — Blaine Lankford
(74) *Attorney, Agent, or Firm* — LANWAY IPR SERVICES; Chun-Ming Shih

(57)    ABSTRACT
Use of a TGF-β small molecule inhibitor in the field of nerve regeneration, for in vitro regeneration and directed differentiation of a variety of nerve cells and brain-like organs. By adding the TGF-β small molecule inhibitor to a set of basal media having clear chemical compositions, pluripotent stem cells can be induced into adult cells derived from a variety of neural stem cells, and the number of induced nerve cells can be greatly increased.

13 Claims, 5 Drawing Sheets

Specification includes a Sequence Listing.

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 1
catgcaggtt gacaccgttg g                                              21

<210> SEQ ID NO 2
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 2
atggattctc ggcagactga ttca                                           24

<210> SEQ ID NO 3
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 3
tctttgcttg ggaaatccg                                                 19

<210> SEQ ID NO 4
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 4
ctgcccgttc aacatcctta g                                              21

<210> SEQ ID NO 5
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 5
ggaagcgaat caatggactc tgg                                            23

<210> SEQ ID NO 6
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 6
gcatcgacat ctgtaccaga cc                                             22

<210> SEQ ID NO 7
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 7
tcaagatgtc cctcagcctg ga                                              22

<210> SEQ ID NO 8
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 8
tggcacaggt gtctcaaggg tag                                             23

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 9
tccctggaga agagctacga                                                 20

<210> SEQ ID NO 10
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 10
agcactgtgt tggcgtacag                                                 20

<210> SEQ ID NO 11
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 11
caagcagagc ggatgtctca gat                                             23

<210> SEQ ID NO 12
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 12
aattgtagag gaggcgaaca ggag                                            24

<210> SEQ ID NO 13
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 13
tgtggtggtg ccttctggag ag                                              22

-continued

```
<210> SEQ ID NO 14
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 14
actgcttgca gcctgagtgt aac                                        23

<210> SEQ ID NO 15
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 15
cgcttcatct cagtgggcta cg                                         22

<210> SEQ ID NO 16
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 16
ccgtcctcgc tctggttgta gta                                        23

<210> SEQ ID NO 17
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 17
aacctgctcc gccgctacaa                                            20

<210> SEQ ID NO 18
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 18
tcctctgcat attcctctgc ctca                                       24

<210> SEQ ID NO 19
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 19
tcatctgtgg agtgggcatc ttca                                       24

<210> SEQ ID NO 20
<211> LENGTH: 24
<212> TYPE: DNA
<213> ORGANISM: Artificial Sequence
<220> FEATURE:
<223> OTHER INFORMATION: Chemically Synthesized
```

-continued

```
<400> SEQUENCE: 20
agcaacttct tggcagcagt atcc                                                      24

<210> SEQ ID NO 21
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 21
ggacaatgac gttgaaacgc agca                                                      24

<210> SEQ ID NO 22
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 22
aaggtcgtaa gcggtttggc taga                                                      24

<210> SEQ ID NO 23
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 23
ctggagagga agattgagtc gc                                                        22

<210> SEQ ID NO 24
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 24
acgtcaagct ccacatggac ct                                                        22
```

NEURAL STEM CELL-INDUCED DIFFERENTIAL MEDIUM AND INDUCTION DIFFERENTIATION METHOD

BACKGROUND OF THE INVENTION

Field of the Invention

The present invention relates generally to the field of biology, in particular to a culture method, a culture medium of ectoderm cells, and an application thereof in nerve injury diseases.

Description of Related Art

The ectoderm is the outermost layer formed during embryonic development. With the initiation of organ development, ectodermal cells gradually differentiate into important systems such as the brain, spinal cord, and sensory organs. Among them, the nervous system is an important system responsible for thinking, emotion, perception, movement and other functions. Compared with diseases such as tumors, there are currently fewer drugs for neurological diseases and the development cycle is long. One of the most important reasons for this is the particularity of multiple primary cells in the epiblast lineage, such as the irreproducibility of primary neurons, which creates a scarcity of in vitro drug screening platforms for drugs in the nervous system.

In addition to being useful for drug screening, the in vitro regeneration of ectodermal cells enables the treatment of several degenerative diseases, such as neurodegenerative diseases. Neurodegenerative diseases are currently common diseases of aging. The treatment and care of neurodegenerative diseases are extremely expensive, and there are no specific drugs available commercially for effective treatment. Neurodegenerative diseases include amyotrophic lateral sclerosis (ALS), Parkinson's disease (PD), Alzheimer's disease (AD) and others. According to the World Health Organization, the number of patients with neurodegenerative diseases in China will exceed 30 million in 2050, and the medical costs are expected to exceed 1 trillion RMB. Currently, the treatment of neurodegenerative diseases mainly includes the following: using drugs to supply or stimulate the production of intracerebral insufficient levodopa, neuronucleus destruction surgery or deep brain electrical stimulation surgery, etc. But none of these treatments can achieve good curative effect, and they bring about "dyskinesias (LID)" or are adverse effects such as "drug efficacy fluctuation" which seriously affect the quality of life.

In addition to neurodegenerative diseases, spinal cord injury (SCI) is a common traumatic disease of the nervous system. According to statistics, the lifetime cost of therapeutic rehabilitation for SCI patients is on average more than 750,000 US dollars, and the USA spends more than 6 billion US dollars annually on SCI patients. The incidence in China is even higher than that in developed countries in Europe and the United States. Expensive treatment costs, long-term rehabilitation treatment and the loss of labor force have a huge impact on individuals and families, and also bring a heavy burden to the society.

The difficulty in the study of neurodegenerative diseases and spinal cord injury lies in the non-renewability of nerve cells in the central nervous system. The scarcity of in vitro disease models is a limiting factor for basic research, whereas neurodegenerative diseases and spinal cord injuries are due to irreversible damage to the central nervous. Nerve cells include neural stem cells, mature neurons, astrocytes, oligodendrocytes and other neuronal cell types. The existing neural cell line resources are limited, most of them are neural system tumor cell lines, and there are unstable factors caused by EB virus in the process of establishing the line. Neural cells are not easy to be passaged in vitro, and neural stem cells from embryos and fetuses are inconvenient to be popularized due to ethical restrictions. At present, although the allogeneic transplantation of neural stem cells has achieved some clinical results, the above factors further hinder the clinical advancement of related diseases.

In 2006, Shinya Yamanaka's group developed a "cocktail" method composed of four transcription factor Oct4, Sox2, KLF4 and c-Myc, which can successfully reprogram terminally differentiated skin fibroblasts into stem cells with differentiated pluripotency. These stem cells are called induced pluripotent stem cells (iPSCs) (Takahashi K., et al., Cell, 2006, 126(4) pp. 663-676; Takahashi K. and Yamanaka. S, Cell, 2007, 131(5) pp. 861-872), These stem cells have a similar differentiation potential to embryonic stem cells. They are able to form the three most basic germ layers of human development: ectoderm, mesoderm and endoderm, and eventually a variety of adult cells. This invention breaks through the ethical limitations of using human embryonic stem cells in medicine, and resolves the issue of immune rejection in cell transplantation therapy, and greatly expands the application potential of ectodermal cells in clinical medicine. The use of pluripotent or multipotent stem cells including embryonic stem cells (ESCs) and induced pluripotent stem cells (iPSCs) as raw materials for epiblast cell induced differentiation can lead to new ideas for clinical treatment, greatly expanding the potential of epiblast cells in clinical medicine.

Taking the nervous system as an example, currently in the field of regenerative medicine, the induction of neural stem cells and neurons mostly adopts the dual SMAD inhibition method (Chambers S M, et. al., NAT biotechnol, 2009, 27 (3): 275-80). The resulting neural stem cells are able to differentiate into other types of neuronal cells by this method. The principle of the method is through the inhibition of BMP and TGF-β pathway to mimic the signal pathway in the early stage of embryonic development and thereby induce the generation of neural stem cells. Among them, LDN-193189 and SB431542 are two widely used chemical small-molecule inhibitors, which respectively act on ALK2 and ALK3 in the BMP4 pathway and ALK5 in the TGF-β pathway to achieve the formation of transplanted endoderm and mesoderm, thereby play a role in inducing ectoderm development and neurogenesis. In this way, induced neural cells can be obtained in the presence of knockout serum replacement (Chambers S M, et. al., Nat Biotechnol., 2013, 30(7):715-720). However, nerve cells obtained by dual SMAD inhibition are often mixed with other incompletely differentiated cell types. This is the result of asynchronous cell differentiation. It affects the effect of transplantation treatment and brings safety concerns. Therefore, how to obtain high-purity differentiated cells is an urgent technical problem to be solved in cell transplantation.

The standard chemical nomenclature of Galunisertib (LY2157299) used herein is 4-(2-(6-methylpyridin-2-yl)-5, 6-dihydro-4h-pyrrolo[1,2-b]pyrazol-3-yl) quinoline-6-carboxamide; Other chemical nomenclatures: 2-(6-Methyl-pyridin-2-yl)-3-(6-Carbamoyl-quinolin-4-yl)-5,6-dihydro-4H-pyrrolo[1,2-b]pyrazole; Or 4-[5,6-Dihydro-2-(6-methyl-2-pyridinyl)-4H-pyrrolo[1,2-b]pyrazol-3-yl]-6-quinolinec arboxamide; Or LY-2157299. LY2157299 is a TGF-β

Receptor I (TGF-β RI, ALK5) small molecule inhibitors. It is currently under phase II clinical evaluation for anticancer activity against liver cancer and glioblastoma (Giannelli G I, Villa E, Cahn M. Transforming Growth Factor-β as a Therapeutic Target in Hepatocellular Carcinoma. Cancer Res. 2014 Apr. 1; 74(7):1890-4), which is achieved by blocking TGF-β signaling pathways to inhibit tumor growth, invasion and metastasis processes. In addition, multiple studies have shown that LY2157299 blocks CTGF production and inhibits neoangiogenesis, resulting in suppression of cancer cell growth. At present, the development direction of this molecule is mainly based on the drug development and treatment of lung cancer, liver cancer and glioblastoma (Pharmaceutics, 2020 May 18; 12(5):459), and no application in the field of nerve regeneration has been disclosed.

The present invention has the following advantages: the present invention uses one chemical small molecule rather than a variety of chemical small molecules to induce nerve cells. Compared with the current internationally accepted induction method of combining a variety of small molecules, the present invention not only greatly saves production costs, but also shows great advantages in purity and yield. The present invention also expands the new function of this small molecule in the field of ectoderm induction. Apart from that, the present invention avoids the use of serum substitutes such as B27, thereby completely eliminating the potential danger posed by the presence of animal derived components during cell culture. Thus, the present invention greatly expands the clinical prospect of neural cell transplantation. The state is stable between multiple batches and the purity is high, which solves the problems of low purity and long cycle in the production process of cell-based drugs. Especially, it can be used for the in vitro screening of drugs for neurological diseases and the treatment of neurodegenerative diseases. Therefore, the present invention has huge economic and social effects.

SUMMARY OF THE INVENTION

In order to solve the deficiencies of the prior art, the present invention provides a serum-free culture medium for inducing neural stem cells and brain-like organoids and a method for inducing differentiation. The above culture medium to induce differentiation of neural stem cells and brain-like organoids includes basal medium and neural inducing compounds.

In order to achieve the above object, the present invention provides the following technical solutions:

The present invention provides an inducing medium for neural stem cells and organoids, wherein the inducing medium consists of basal medium and 10 nM-100 μM neuroinductive compounds; The basal medium contains Dulbecco's modified Eagle/F12 medium, minimum essential medium non-essential amino acids, sodium chloride, sodium selenite, insulin and recombinant human transferrin.

Preferably, the basal medium consists of Dulbecco's modified Eagle/F12 medium, 1% minimum essential medium non-essential amino acids, 0.1 g/L-0.8 g/L sodium chloride, 13.6 μg/L sodium selenite, 20 ng/mL-42 μg/mL insulin and 50 ng/mL-180 ng/mL recombinant human transferrin.

More preferably, the basal medium contains 0.5 g/L sodium chloride, 13.6 μg/L sodium selenite, 22 μg/mL insulin and 100 ng/mL recombinant human transferrin.

Preferably, the neuroinductive compounds are substances that act on the BMP or TGF signal transduction pathway.

More preferably, the substance acting on the TGF signal transduction pathway is TGF-β inhibitor.

More preferably, the TGF-β inhibitor is 4-[2-(6-methylpyridin-2-yl)-5,6-dihydro-4H-pyrrolo[1,2-b]pyrazol-3-yl] quinoline-6-carboxamide.

More preferably, the concentration of the TGF-β inhibitor is 12.5 μM.

In one embodiment, the present invention provides a method for inducing the formation of neural stem cells, wherein the inducing medium described above is used for adherent culture of pluripotent stem cells.

Preferably, the pluripotent stem cells are mammalian pluripotent stem cells.

More preferably, the pluripotent stem cells are human pluripotent stem cells.

Preferably, the adherent culture is performed in the presence of a basement membrane preparation.

More preferably, the basement membrane preparation is one or a combination of two or more of Matrigel, laminin, and vitronectin.

The present invention also provides the application of neural stem cells obtained by the method described above to prepare medications for treating nerve damage.

In another embodiment, the present invention provides a method for further differentiation of neural stem cells into neuronal cells, wherein the neural stem cells are obtained by the method described above, and inducing differentiation substances are added to the basal medium described above to culture until neurons form.

Preferably, the inducing differentiation substances are CHIR99021, SU5402, and DAFT, and the neural stem cells further differentiate into nociceptor neurons.

Preferably, the inducing differentiation substances are Purmorphamine and TGF-β3, and the neural stem cells further differentiate into dopaminergic neurons.

Preferably, the inducing differentiation substance is retinyl acetate, and the neural stem cells further differentiate into photoreceptor neurons.

In another embodiment, the present invention provides a type of brain-like organs inducing medium, which is consisting of the neural stem cells inducing medium described above and an additive; wherein the additive is ROCK inhibitor Y-27632.

In another embodiment, the present invention provides a method for inducing the formation of brain-like organs, characterized in that the pluripotent stem cells are cultured by using the brain-like organs inducing medium described above; Replace the medium with brain-like organs inducing medium without Y-27632 the next day, change the medium daily, and on the 10th day, replace it with the basal medium described above, and add 2% B27 cell culture additive to cultivate until the 120th day.

The present invention also provided the application of brain-like organs obtained by the method described above to the screening of drugs for neurological diseases.

The invention provides an application of an anti-tumor small molecule inhibitor in the in vitro development of ectoderm, in particular to the combination of the compound and basic culture medium, as well as the culture and clinical application of the combination in a variety of nerve cells.

The present invention provides steps for preparing human induced neural stem cells: pluripotent stem cells are cultured by monolayer adherent culture in a serum-free sensory nerve-inducing medium. The above-mentioned serum-free medium contains chemical small molecules, amino acids, inorganic salts and other components used in the present invention, but does not contain serum, BMP or TGF signal transduction pathway substances and other components. After 20 days of adherent culture with this serum-free nerve-inducing medium, neural stem cells with uniform arrangement of neural rosettes were obtained.

In specific embodiments, the substances acting on the BMP signal transduction pathway include one or more proteins that are freely arranged in combination by each of the following: BMP2, BMP4, BMP4, Smad1, Smad5, smad8. Wherein, substances that act on the TGF transduction pathway include one or more proteins that are free to combine by each of the following: Activin, TGF-β, Nodal, Smad2, Smad3.

In a particular embodiment, the adherent culture is carried out in the presence of a basement membrane preparation. The basement membrane preparation of the present invention which can form a thin film consisting of extracellular matrix molecules on the surface of the culture vessel. The thin film can provide an in vivo like environment for cell morphology, growth and differentiation, as well as motility, etc. In specific embodiments, the basement membranes described above are one or more combinations of base adhesive (Matrigel, STEMCELL Technologies), laminin, and vitronectin.

The serum-free medium in the present invention means that it does not contain serum directly separated from blood. Serum is the transparent liquid part of plasma, which does not contain fibrinogen or blood cells and remains liquid after blood coagulation. Serum-free medium may contain serum substitutes, and examples of serum substitutes include purified substances such as serum albumin, transferrin, fatty acids, etc.

In a specific embodiment, the adherent culture in steps 1 to 3 is preferably carried out with a basement membrane. The basement membrane of the present invention which can form a thin film consisting of extracellular matrix molecules on the surface of the culture vessel. The thin film can provide an in vivo like environment for cell morphology, growth and differentiation, as well as motility, etc. In specific embodiments, the basement membranes described above are one or more combinations of base adhesive (Matrigel, STEMCELL Technologies), laminin, and vitronectin.

Methods for preparing drugs for treating nerve injury can refer to published methods for using embryonic stem cells as drugs for treating nerve injury, such as the work of Okada et al. (Okada Y, Matsumoto A, Shimazaki T, Enoki R, Koizumi A, Ishii S, Itoyama Y, Sobue G, Okano H. Stem Cells. 2008 vol. 26, pp. 3086-98).

In addition to pluripotent cells of human origin, drugs used to treat nerve injuries can contain other components, such as buffers containing salts and or antibiotics, or neural tissue as a therapeutic target (e.g., the central or peripheral nervous system such as the brain, spinal cord, etc.). In addition, the target disease for treatment is not limited to any specific symptom, including traumatic diseases such as spinal cord injury (SCI), neurodegenerative diseases (e.g., amyotrophic lateral sclerosis, Parkinson's disease, Alzheimer's disease, progressive supranuclear palsy, Huntington's disease, multiple system atrophy, and spinocerebellar degeneration), neuronal cell necrosis caused by cerebral infarction and intracerebral hemorrhage, etc. The target disease for treatment is also not limited to any specific etiology, including primary causes associated with injury, cerebral infarction, etc., and secondary causes such as infections, tumors, etc., as long as diseases or pathological symptoms belonging to neuronal cell damage are included.

Definitions

Neural Stem Cells, NSCs:

Neural stem cells, a class of mother cells with division potential and self-renewal capacity, are a population of cells that are sufficient to supply the bulk of brain tissue cells. It can generate various types of cells of the nervous tissue, including neurons, oligodendrocytes, and astrocytes, through unequal division. According to the present invention, neural stem cells can be induced neural stem cells (iNSC).

Neural Rosette:

Neurulation belongs to the early neurogenesis process and is considered to be a critical stage in human embryonic development. The neurula develops into the brain, spinal cord, and other nervous systems under the exquisite regulation of various factors. Neurulation is described as the production of a rosette like neural stem cell structure within a clump of cellular tissue, i.e., a neural rosette structure symbolizes a neurula.

Beneficial Effects:

The culture medium provided by the present invention does not contain serum, which solves the problem that the animal derived culture method restricts the use of stem cells in the clinic. The above culture medium is suitable for culturing neural stem cells, including but not limited to induced pluripotent stem cells.

The culture medium provided by the invention is characterized by simplicity, safety and efficiency. Directed differentiation of induced stem cells into neural stem cells was achieved by using a single small molecule inhibitor.

The neural stem cells induced to differentiate by the method provided by the invention have the ability to differentiate into neurons and organ like cells, which can not only be used as materials for clinical research and clinical treatment, but also be used for screening research of drugs for nervous system diseases, with huge economic and social effects.

BRIEF DESCRIPTION OF THE FIGURES

Comparison of differences between the method of the invention (LY inducing method) and the control method (LSB inducing method) in the induction process of neural stem cells. FIG. 1a shows the neural rosette structure induced by a variety of small molecule inhibitors (LSB inducing method); FIG. 1b shows the neural rosette structure produced by neural stem cell induction (LY inducing method) using LY2157299 alone; FIG. 1c shows the difference in the number of neural stem cells obtained by the two methods.

FIG. 2 Screening results of core components of basic culture medium in the method of the invention. FIG. 2a shows the effect of different concentrations of sodium chloride on the osmotic pressure of the culture system. Excessive concentration will lead to osmotic pressure exceeding cell tolerance. FIG. 2b shows the effect of different concentrations of insulin on cell growth (Cyquant experiment). Insulin concentration was positively correlated with cell viability. FIG. 2c shows the effect of different concentrations of recombinant human serum albumin on cell growth (Cyquant experiment). The concentration of recombinant human serum albumin was positively correlated with cell viability.

FIG. 3a represents the reconstruction of the structure of the neural rosette after in vitro passage of neural stem cells obtained by using the LSB inducing method; FIG. 3b represents that neural stem cells Obtained by using the LSB inducing method express the specific marker Pax6; FIG. 3c represents that the neural stem cells obtained by using the LSB inducing method expressed the specific marker Nestin; FIG. 3d represents the channel integration picture of FIGS. 3a-3c; FIG. 3e represents the reconstruction of the structure of the neural rosette after in vitro passage of neural stem cells Obtained by using the LY inducing method; FIG. 3f represents neural stem cells obtained by using LY inducing method expressed specific marker Pax6; FIG. 3g represents that the neural stem cells obtained by using the LY inducing method expressed the specific marker Nestin; FIG. 3h represents the channel integration picture of FIGS. 3e-3g; FIGS. 3i-3k show the difference in expression of neural stem cell markers during neural stem cell formation using Q-PCR comparing the LY inducing method with the LSB control inducing method.

FIG. 4a shows neural stem cells obtained by using a multi molecular control (LSB inducing method, designated CK); FIG. 4b shows chemical induction using LY2157299 at 0 nM; FIG. 4c shows chemical induction using LY2157299 at 20 nM; FIG. 4d shows chemical induction using LY2157299 at 12.5 μM; FIG. 4e shows chemical induction using LY2157299 at 25 μM; FIG. 4f shows the regulation of Pax6 by different concentrations of LY2157299 during induction compared using Q-PCR analysis; FIG. 4g shows the regulation of apoptosis gene CASP3 using Q-PCR analysis comparing different concentrations of LY2157299 during the inducing process.

FIGS. 5a-5c show induced neural stem cells obtained through LY2157299 as well as further differentiation of the resulting nociceptor neurons; FIG. 5A shows that nociceptor neurons derived by this method express the nociceptor neuron specific marker SCN11A; FIG. 5b shows that nociceptor neurons derived by this method express the nociceptor neuron specific marker Nestin; FIG. 5c shows the integration of two fluorescence channels in FIG. 5a and FIG. 5b, FIGS. 5d-5f show the induced neural stem cells obtained by LY2157299 along with further differentiation of the resulting dopaminergic neurons; FIG. 5d shows that the dopaminergic neurons obtained by this method express the specific marker Pitx3 of mature dopaminergic neurons; FIG. 5e shows that dopaminergic neurons derived by this method express the mature dopaminergic neuron specific marker TH; FIG. 5f shows the integration of two fluorescence channels in FIG. 5d and FIG. 5e; FIGS. 5g-5i show the induced neural stem cells obtained through LY2157299 along with further differentiation of the resulting photoreceptor neurons; FIG. 5g shows that the photoreceptor neurons obtained by this method express the photoreceptor neuron specific marker OPSIN; FIG. 5h shows that the photoreceptor neurons derived by this method express the photoreceptor neuron specific marker CRX; FIG. 5I shows the integration of two fluorescence channels in FIG. 5g and FIG. 5h.

FIG. 6a-6d indicate that neural stem cells obtained with LY2157299 were significantly lower than human induced pluripotent stem cells in the expression of CD4, HLA-A, HLA-C, and HLA-DPB1, respectively.

FIG. 7a is a negative control without antibody staining, and FIG. 7b is the HLA-DR detection result of neural stem cells induced by LY2157299. FIG. 7a-1 shows the use of SSC and FSC channels to exclude cell debris and other particulate impurities and determine the cell populations for analysis by gating; FIGS. 7a-2 and 7a-3 show the use of blank fluorescence channels and cell morphology to analyze cells respectively; FIG. 7a-4 shows the use of two blank fluorescence channels to analyze cells; FIG. 7b-1 shows the use of SSC and FSC channels to exclude cell debris and other particulate impurities and determine the cell populations for analysis by gating; FIG. 7b-2, 7b-3 indicate that cells were analyzed using CD45 PerCP (Abcam, cat. No. ab157309), HLA-DR FITC (CST, cat. No. 54126) channels and cell morphology, respectively; FIG. 7b-4 shows the analysis of cells using two fluorescent channels CD45 PerCP and HLA-DR FITC. The results showed that the HLA-DR antigen expression of the neural stem cells induced by LY2157299 was negative.

FIG. 8a shows the cerebral organoids formed by the LSB inducing method (DSO); FIG. 8b shows the cerebral organoids formed by the LY inducing method (D50); FIG. 8c shows a comparison of the spontaneous discharge numbers of cerebral organoids prepared by different methods by using a multichannel electrode system; FIG. 8d shows a comparison of the spontaneous firing frequency of cerebral organoids prepared by different methods by using a multichannel electrode system; FIG. 8e shows the diameter of organoids prepared by different methods (n=10); FIG. 8f-8g show the analysis of gene expression differences obtained by different organoid preparations by using Q-PCR.

DETAILED DESCRIPTION OF THE INVENTION

Figures 1, 2:
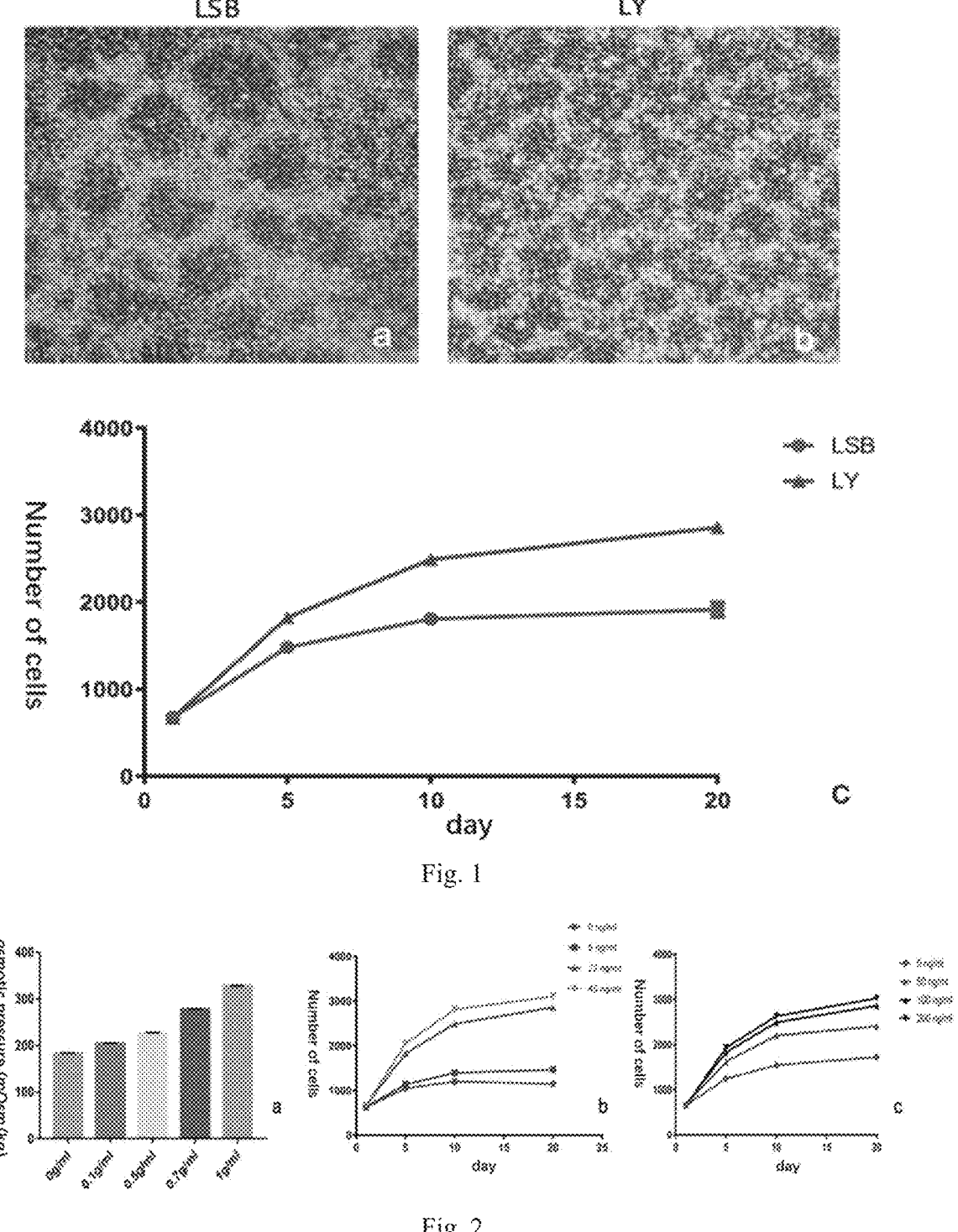

The present invention will be further described below with reference to the accompanying drawings and specific embodiments, and the protection content of the present invention is not limited to the following embodiments. It should also be understood that the terms used in the embodiments of the present invention are for describing specific embodiments, rather than for limiting the protection scope of the present invention. Variations and advantages that can occur to those skilled in the art without departing from the spirit and scope of the inventive concept are all included in the present invention, and the appended claims and any equivalents thereof are within the protection scope of the present invention. In the present specification and claims, the singular forms "a," "an," and "the" include plural referents unless the context clearly dictates otherwise. The experimental methods that do not specify specific conditions in the following examples are the general knowledge and common knowledge of those skilled in the art, or according to the conditions suggested by the manufacturer. Unless otherwise specified, all materials and reagents used in the examples are commercially available products.

EXAMPLES

Example 1: Preparation of Neural Stem Cell Inducing Medium

The formula of neural inducing basal medium (hereinafter referred to as NouvNeu001): Dulbecco's modified Eagle/F12 medium (DMEM/F12), 1% minimum essential medium non-essential amino acids (MEM non-essential amino acids, Thermo Fisher, Cat. No.: 11140076), sodium chloride (0.5 g/L), sodium selenite (13.6 μg/L), insulin (22 μg/mL), recombinant human transferrin (100 ng/ml).

The neural stein cell inducing medium used in the present invention is prepared by adding 55 nM-24 µM LY2157299 (Selleck, S2230) to NouvNeu001 basal medium, and the final concentration is preferably 300 nM, 500 nM, 700 nM, 900 nM, 1 µM, 5 µM, 5 µM, 10 µM, 12.5 µM, 15 µM, 17 µM, 20 µM or 22 µM, most preferably 12.5 µM. The above-mentioned medium is referred to as the LY inducing medium for short, and the experimental group using this medium is referred to as the LY inducing method below.

The medium used for the control experiments is prepared by supplementing NouvNeu001 basal medium with 100 nM LDN-193189 (Selleck, S2618) and 10 µM SB431542 (Selleck, S1067). The above-mentioned medium is referred to as the LSB inducing medium for short, and the experimental group using this medium is referred to as the LSB inducing method hereinafter.

Example 2: Induction and Identification of Neural Stem Cells 2.1 Chemical Induction of Neural Stem Cells:

Human pluripotent stem cells include embryonic pluripotent stem cells, such as the H19 cell line and human induced pluripotent stem cells. Wherein, the human induced pluripotent stem cells used in the present invention are obtained from the reprogramming of CD34$^+$ cells, which refers to "reprogramming culture medium and reprogramming induced pluripotent stem cell culture method" (the method in the patent ZL201910050800.7).

Human pluripotent stem cells are used to coat T25 cell culture flasks with Matrigel (STEMCELL Technologies), and then placed in a 37° C. incubator for more than one hour after plating. Follow 1×10$^6$ Cells were seeded in T25 flasks for expansion and passage.

For neural induction, use 50 µg/mL poly-lysine (SIGMA, Cat. No.: P6407) to coat a 6-well culture plate, and incubate at 37° C. for more than 3 hours after plating; then use 5 µg/mL Laminin (SIGMA ALDRICH, Cat. No.: 12020) for further coat, and then place in a 37° C. incubator to incubate for more than 3 hours. When pluripotent stem cells reached 70% coverage, they were digested with EDTA at 37° C. for 5 min, and DMEM was used to stop cell digestion. Cells are washed and centrifuged at 2×10$^5$ the proportions of each flask and are re-seeded in T25 plates. Neural induction is performed using the medium of the present invention in combination with the neural inducing compound, and the medium is changed every day until the neural stem cell rosette is formed. As shown in FIG. 1a and FIG. 1b, compared with the multi-molecule inducing method (LSB induction method), the single-molecule inducing method used in the present invention (LY inducing method) formed small and uniform neural rosette structures. This result shows that compared with the multi-molecule inducing method used in the control, the single-molecule inducing method provided by this method produces more uniform induction results, while the rosette structures produced by the control experiment have different sizes. And in the same culture period, there are still some parts that do not form a neural rosette structure in the control group. Therefore, the single-molecule inducing method provided by this method can induce pluripotent stem cells to form neural rosette structures more efficiently and uniformly.

2.2 Concentration Identification of Key Components in the Inducing System:

The Cyquant assay was used to perform the quantitative detection of cell viability, thus investigating the effect of LY2157299 on the physiological state of the cells during long-term culture of the cells; Among them, the LSB method was used as the control group. 96-well light-tight cell culture plates were coated; after the coating was complete, cells were seeded separately at 5×10$^4$ cell number per well and three sets of parallel replicates were set (the average of three sets was calculated as data) to repeat the procedure of example 2.1. Wherein, the culture procedures described previously were incubated at 37° C. with 5% CO$_2$. Samples were taken on days 1, 5, 10, 15 and 20 for cell viability assay using CyQuant Kit (Invitrogen, cat. No: X12223). The aforementioned assay was operated according to the instructions with a Spectramax i3 Multi-Mode Microplate Reader (VWR, model number: ID3-STD) for data reading. The results are shown in FIG. 1c: CyQuant assay showed that LY2157299 induced more number of neural cells compared with LSB method, which illustrated that LY2157299 possessed more proliferative activity during the inducing process.

The CyQuant assay was also used to perform quantitative assays of cell viability, thereby investigating the effect of different concentrations of recombinant insulin and recombinant serum albumin on the physiological state of the cells during long-term culture, and the results are shown in FIG. 2b and FIG. 2c: Both recombinant insulin and recombinant serum albumin concentrations were positively correlated with the rate of cell proliferation. Combined with cost factors, the range of recombinant insulin and recombinant serum albumin used by the present invention falls within the range of optimal use.

A fully automated freezing point osmometer (FM-8P, Shanghai Yida Instruments Co., Ltd.) was used to detect the effects of different concentrations of sodium chloride on the osmolality of the culture system, and the specific operations were enrolled in the product instructions (FM-8P, Shanghai Vida Instruments Co., Ltd.). The test results are detailed in FIG. 2a. The results illustrate a linear increase with the concentration of sodium chloride and the osmotic pressure of the culture system. However, when the concentration reached 1 µg/mL, the osmolality of the culture system already exceeded the cell culture limit of 320 mOsm/kg. The above experimental results show that the concentration of sodium chloride used in the present invention is the one most suitable for cell culture.

2.3 Fluorescence Immunoassay of Markers of Neural Stem Cells:

The neural stem cells obtained from the LY inducing method and LSB inducing method, respectively, were identified by immunofluorescence staining, and then the cells were fixed with 4% paraformaldehyde for 40 min at room temperature and, subsequently washed twice with DPBs buffer; after permeabilization of the cells with 0.1% Triton X-100 for 5 min, they were washed twice with DPBs buffer; Cells were then incubated overnight at 4° C. with DPBs buffer containing 10% horse serum and, 0.1% Triton X-100; Cells were then washed with DPBs buffer and primary antibody was diluted in DPBs buffer containing 2% horse serum and 0.1% Triton X-100 and incubated for 2 hours at 37° C.; After the cells were washed with DPBs buffer, the secondary antibody was diluted with DPBs buffer containing 2% horse serum and 0.1% Triton X-100, and the cells were incubated at 37° C. for 2 h. Then the cells were washed three times and photographed using Leica DMi8. The antibody usage details are shown in Table 1 and the results are shown in FIG. 3a-3h. The result shows that, compared with the LSB induction method, the LY inducing method enables the generation of neural rosette structures from pluripotent stem cells and the cells can express the neural stem cell markers Pax6 and Nestin.

TABLE 1

| antibodies used for immunofluorescence staining of cells | | | |
|---|---|---|---|
| primary antibody | | secondary antibody | |
| antibody | Concentration | antibody | Concentration |
| Anti-PAX6-antibody (Abcam) | 1:200 | Goat anti rabbit IgG (H + L), Alexa Fluor 488 (Invitrogen A11034) | 1:1000 |
| Anti-Nestin antibody (Millipore) | 1:400 | Donkey anti mouse IgG (H + L), Alexa Fluor 568 (Invitrogen A11004) | 1:1000 |

2.4 Transcriptional Level Identification of Neural Stem Cells:

Transcriptional changes of different marker genes during induction from pluripotent stem cells to neural stem cells were detected by using Q-PCR. The induced pluripotent stem cells used in this example are neural stem cells derived by LY inducing method and LSB inducing method, respectively. Neural stem cells were prepared as described previously using Rneasy Mini or Micro Kit (QIAGEN) for total RNA extraction, in which 1 mg RNA was used to synthesize cDNA with superscript III First-Strand Synthesis System (Invitrogen).

SYBR Premix Ex Taq (TaKaRa) and Thermal Cycler Dice Real Time System TaKaRa) were used to perform labeling and reactions for Quantitative PCR, with beta-Actin as internal reference. All the above data were analyzed with the delta-Ct method. Each set of trials was tested using three sets of replicates, and variance statistics were performed. The primer sequences used to identify the encoding genes for the different cell markers are shown in Table 2. The results are shown in FIG. 3*i*-3*k*: the neural stem cells obtained by the LY inducing method and the LSB inducing method both expressed the neural stem cell-specific markers Sox2, Pax6 and Nestin, and the LY inducing method showed an increase in the expression of NSCs markers compared to the LSB inducing method.

Figures 3, 4:
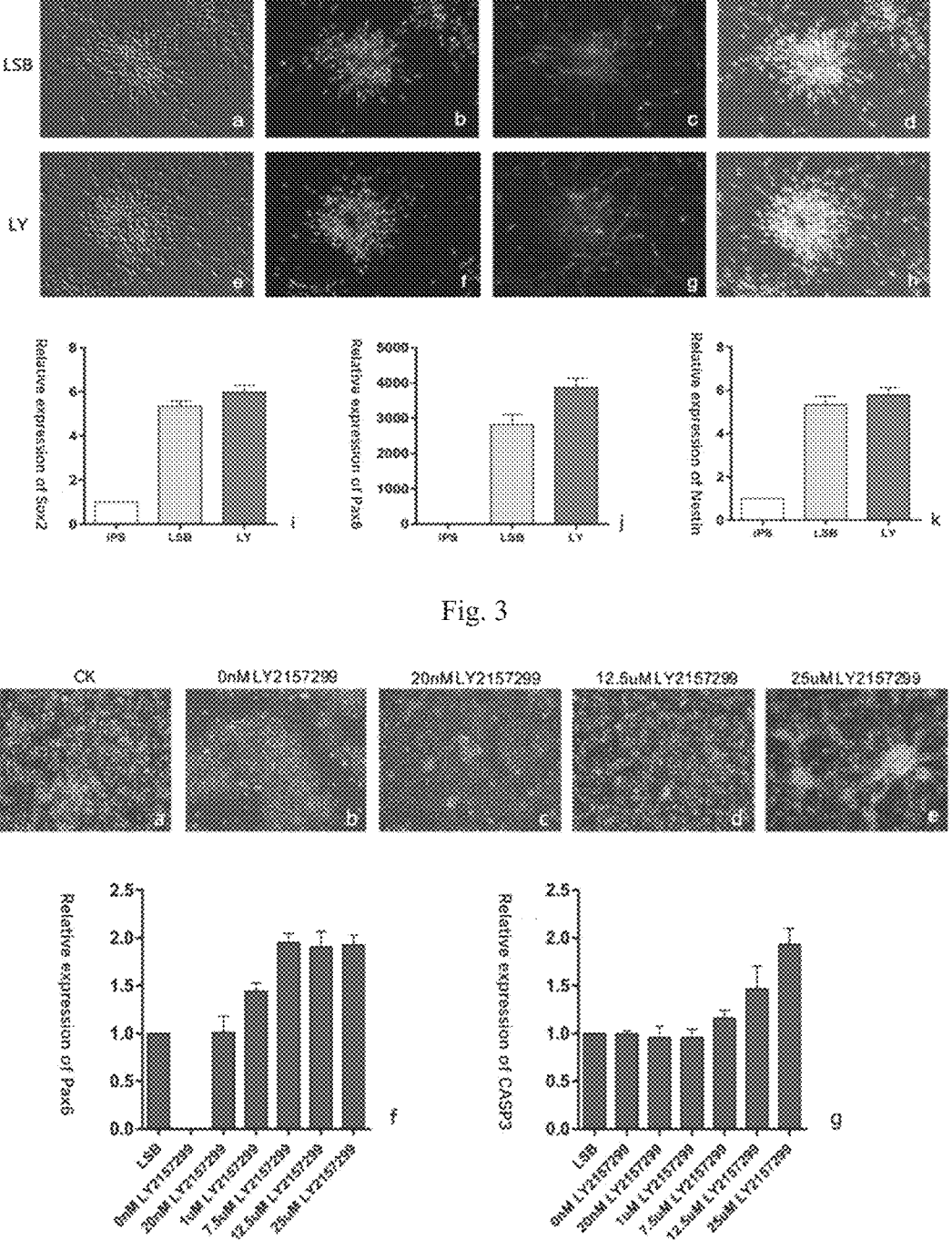
FIG. 3 molecular identification of the cells obtained by by the present method (LY inducing method) versus the control method (LSB inducing method).
FIG. 4 different concentrations of LY2157299 were used for chemical induction of NSCs.

Through the above method, different concentrations of LY2157299 in NouvNeu001 basal medium were added for concentration screening, and the results are shown in FIG. 4*b*-4*e*: FIG. 4*b* shows that the absence of LY2157299 will result in a failure of the cells to differentiate into ectodermal cells; FIG. 4*c* shows that using 20 nm LY2157299 for chemical induction, a mixed population of cells including neural cells was obtained; FIG. 4*d* shows that chemical induction with 12.5 μM LY2157299 resulted in a uniform cell population, and the cells had typical neural stem cell morphology, similar to the control (4*a*); FIG. 4*e* shows that using 25 μM LY2157299 chemical induction, a mixed population of neural cells was obtained, while some cells formed longer axons and cells showed signs of stress with intracellular vacuoles. From the above results, it is known that the differentiation is not complete under the low concentration condition, and many different types of cells can be seen. However, neural stem cells obtained in high concentration condition are easily differentiated and cell stress appears. Transcript levels further demonstrate that the concentrations used herein are optimal (FIG. 4*f*-4*g*): FIG. 4*f* shows that the concentration of LY2157299 is positively correlated with Pax6 expression; FIG. 4*g* shows that the concentration of LY2157299 is positively correlated with apoptosis. The above results indicate either too low or too high concentrations of LY2157299 adversely affect neural induction.

TABLE 2

| Different marker gene primers during the induction of pluripotent stem cells to neural stem cells | | |
|---|---|---|
| Gene | Primer sequences | SEQ ID NO. |
| SOX2-F | CATGCAGGTTGACACCGTTGG | SEQ ID NO: 1 |
| SOX2-R | ATGGATTCTCGGCAGACTGATTCA | SEQ ID NO: 2 |
| PAX6-F | TCTTTGCTTGGGAAATCCG | SEQ ID NO: 3 |
| PAX6-R | CTGCCCGTTCAACATCCTTAG | SEQ ID NO: 4 |
| CASP3-F | GGAAGCGAATCAATGGACTCTGG | SEQ ID NO: 5 |
| CASP3-R | GCATCGACATCTGTACCAGACC | SEQ ID NO: 6 |
| Nestin-F | TCAAGATGTCCCTCAGCCTGGA | SEQ ID NO: 7 |
| Nestin-R | TGGCACAGGTGTCTCAAGGGTAG | SEQ ID NO: 8 |
| ACTIN-F | TCCCTGGAGAAGAGCTACGA | SEQ ID NO: 9 |
| ACTIN-R | AGCACTGTGTTGGCGTACAG | SEQ ID NO: 10 |

Example 3: Identification of Differentiation Function of Neural Stem Cells

The neural stem cells obtained by the LY inducing method in Example 2 were subjected to directed differentiation in NouvNeu001 basal medium. For neuronal differentiation, use 50 μg/mL polylysine (SIGMA ALDRICH, Cat. No.: P6407) to coat a 6-well culture plate, and place the plate in a 37° C. incubator and incubate for more than 3 hours until cells are seeded.

3.1 Nociceptor Neuron Differentiation:

The neural stem cells obtained in example 2 were seeded at a density of $1\times10^5$ the ratio per flask was inoculated in T25 flasks, and 3 μM CHIR99021 (Selleck, Cat. No.: S2924), 10 μM SU5402 (Tocris, Cat. No.: 3300/1), 10 μM DAPT (Selleck, Cat. No.: 52215) were added to NouvNeu001 basal medium. Fresh medium was replaced every 3 days until day 21. The above cultures were incubated at 37° C. with 5% $CO_2$. The experimental results demonstrate that the resulting neural stem cells in example 2 have axonal structures upon differentiation and are able to express the nociceptor neuronal markers SCN11A and Nestin (FIG. 5*a*-5*c*). FIG. 5*a* shows that nociceptor neurons derived by further differentiation of induced neural stem cells obtained through LY2157299 express the nociceptor neuron specific marker SCN11A, FIG. 5*b* shows that nociceptor neurons derived by this method express the nociceptor neuron specific marker Nestin; FIG. 5*c* shows the integrated pictures of two kinds of fluorescence channels in FIGS. 5*a* and 5*b*.

3.2 Induction of Dopamine Neuron Cells:

The neural stem cells obtained in example 2 were seeded at a density of $1\times10^5$ the ratio per flask was inoculated in T25 flasks, and 1 μM Purmorphamine Sellek, Cat. No.: S3042) and 1 mg/mL TGF-β3 (Novoprotein, Cat. No.: CJ44) were added to NouvNeu001 basal medium to culture neural stem cells. Fresh medium was replaced every 3 days until day 30.

The above cultures were incubated at 37° C. with 5% $CO_2$. Experimental results showed that the resulting neural stem cells in example 2 had axonal structures upon differentiation and could express the mature dopaminergic neuron specific markers Tyrosine Hydroxylase (TH) and Pitx3 (FIG. 5d-5f). FIG. 5d shows that dopaminergic neurons obtained by LY2157299 induced neural stem cells to further differentiate and the differentiation products can express mature dopaminergic neuron specific marker Pitx3; FIG. 5e shows that dopaminergic neurons derived by this method express the mature dopaminergic neuron specific marker TH; FIG. 5f shows the integrated pictures of two kinds of fluorescence channels in FIGS. 5d and 5e.

3.3 Photoreceptor Neuron Differentiation:

The neural stem cells obtained in example 2 were seeded at a density of $1 \times 10^5$ the ratio per flask was inoculated in T25 flasks, and 0.5 μM retinyl acetate (SIGMA ALDRICH, Cat. No.: R7782) was added to NouvNeu001 basal medium. Fresh medium was replaced every 3 days until day 21. The above cultures were incubated at 37° C. with 5% $CO_2$. Experimental results demonstrated that the resulting neural stem cells in example 2 had axonal structures and could express the photoreceptor neuronal markers OPSIN and CRX after differentiation (FIG. 5g-5i). FIG. 5g shows that photoreceptor neurons obtained by LY2157299 induced neural stem cells to further differentiate and the differentiation products can express the photoreceptor neuron specific marker OPSIN; FIG. 5h shows that photoreceptor neurons derived by this method express the photoreceptor neuron specific marker CRX; FIG. 5i shows the integrated pictures of two kinds of fluorescence channels in FIGS. 5g and 5h.

After induction and differentiation, the cells were harvested and identified by immunofluorescence staining: cells were fixed with 4% paraformaldehyde at room temperature for 40 minutes, washed twice with DPBS buffer; then permeabilized with 0.1% Triton X-100 for 5 minutes, and buffered with DPBS The cells were then washed twice with DPBS buffer containing 10% horse serum and 0.1% Triton X-100 at 4° C. overnight; the cells were washed with DPBS buffer and then washed with 2% horse serum and 0:1% Triton X-100. The secondary antibody was diluted with 100 DPBS buffer, incubated at 37° C. for 2 hours, washed three times, and photographed with Leica Dmi8, Antibody usage details are shown in Table 3.

TABLE 3

Antibodies used for directed differentiation

| primary antibody | | secondary antibody | |
|---|---|---|---|
| antibody | Concentration | antibody | Concentration |
| Anti-SCN11A-antibody (Abcam) | 1:200 | Goat anti rabbit IgG(H + L), Alexa Fluor 488 (Invitrogen A11034) | 1:1000 |
| Anti-Tuj antibody (Millipore) | 1:200 | Donkey anti mouse IgG(H + L), Alexa Fluor 568 (Invitrogen A11004) | 1:1000 |
| Anti- Tyrosine Hydroxylase-antibody (Santa Cruz) | 1:400 | Donkey anti mouse IgG(H + L), Alexa Fluor 568 (Invitrogen A11004) | 1:1000 |
| Anti-Pitx3 antibody (Invitrogen 38-2850) | 1:200 | Goat anti rabbit IgG(H + L), Alexa Fluor 488 (Invitrogen A11034) | 1:1000 |
| Anti-Opsin antibody | 1:200 | Goat anti rabbit IgG(H + L), | 1:1000 |

TABLE 3-continued

Antibodies used for directed differentiation

| primary antibody | | secondary antibody | |
|---|---|---|---|
| antibody | Concentration | antibody | Concentration |
| (Millipore) | | Alexa Fluor 568 (Invitrogen A11011) | |
| Anti-CRX antibody (Novusbio) | 1:100 | Donkey anti mouse IgG(H + L), Alexa Fluor 488 (Invitrogen A21202) | 1:1000 |

The above results indicated that the neural stem cells obtained by LY inducing method had the differentiation ability of a variety of neurons.

Figures 5, 6:
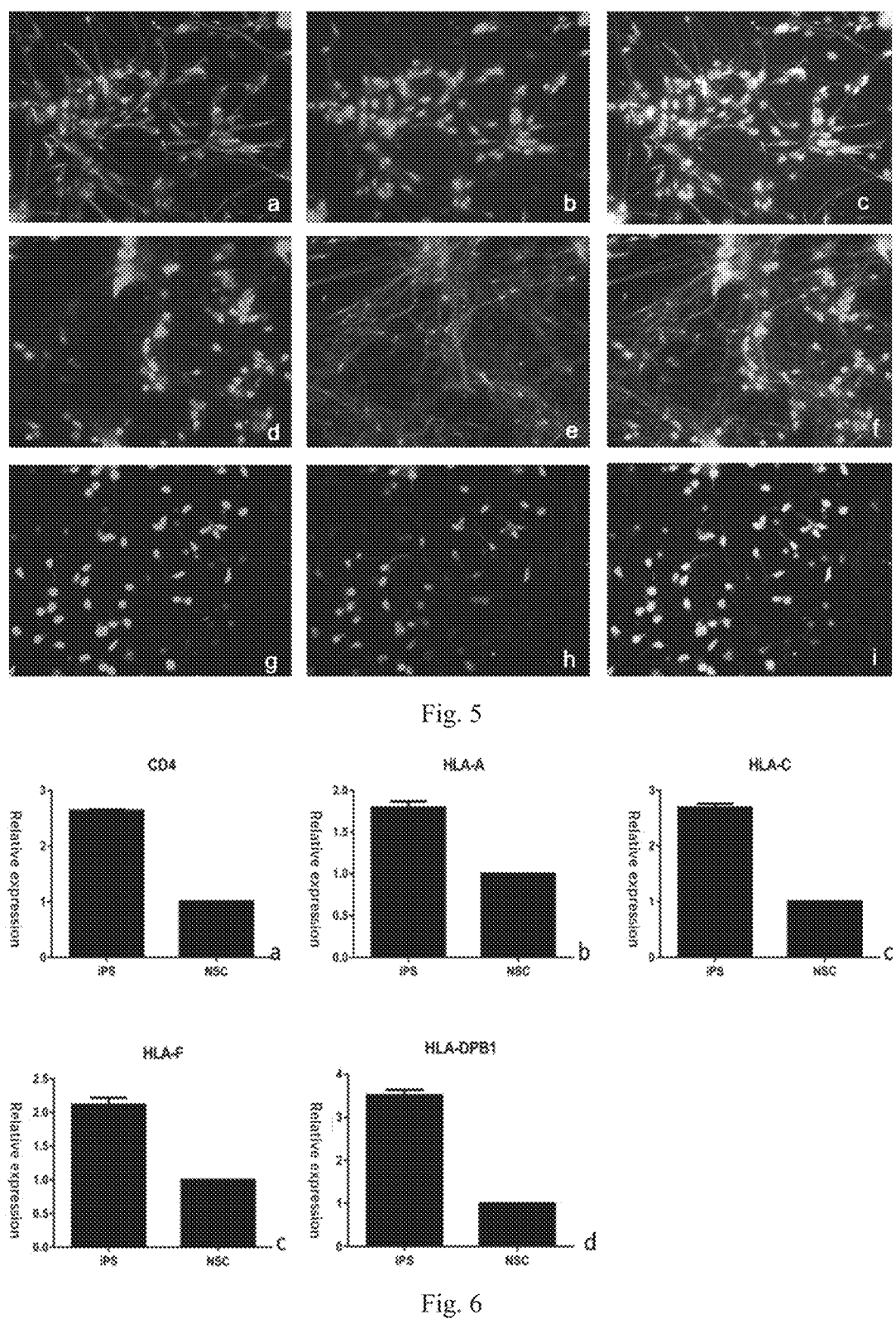
FIG. 5 differentiation ability identification of neural stem cells obtained by LY inducing method.
FIG. 6 MHC related gene expression analysis of neural stem cells Obtained by LY inducing method.

Example 4: Effect of LY2157299 on MHC formation 4.1 Q-PCR Detection:

The major histocompatibility complex (MHC) genes of neural stem cells induced by LY2157299 was detected by Q-PCR method, and pluripotent stem cells (iPS) were used as control. The primer sequences are shown in Table 4, and test results are shown in FIG. 6: the MHC associated genes CD4, HLA-A, HLA-C, hla-f, and HLA-DPB1 were expressed at extremely low levels in neural stem cells obtained by LY2157299 induction compared with human pluripotent stem cells.

TABLE 4

Primers of immune system related genes

| Gene | Primer sequences | SEQ ID NO. |
|---|---|---|
| CD4-F | CAAGCAGAGCGGATGTCTCAGAT | SEQ ID NO: 11 |
| CD4-R | AATTGTAGAGGAGGCGAACAGGAG | SEQ ID NO: 12 |
| HLA-A-F | TGTGGTGGTGCCTTCTGGAGAG | SEQ ID NO: 13 |
| HLA-A-R | ACTGCTTGCAGCCTGAGTGTAAC | SEQ ID NO: 14 |
| HLA-C-F | CGCTTCATCTCAGTGGGCTACG | SEQ ID NO: 15 |
| HLA-C-R | CCGTCCTCGCTCTGGTTGTAGTA | SEQ ID NO: 16 |
| HLA-F-F | AACCTGCTCCGCCGCTACAA | SEQ ID NO: 17 |
| HLA-F-R | TCCTCTGCATATTCCTCTGCCTCA | SEQ ID NO: 18 |
| HLA-DPB1-F | TCATCTGTGGAGTGGGCATCTTCA | SEQ ID NO: 19 |
| HLA-DPB1-R | AGCAACTTCTTGGCAGCAGTATCC | SEQ ID NO: 20 |
| ACTIN-F | TCCCTGGAGAAGAGCTACGA | SEQ ID NO: 9 |
| ACTIN-R | AGCACTGTGTTGGCGTACAG | SEQ ID NO: 10 |

Figure 7:
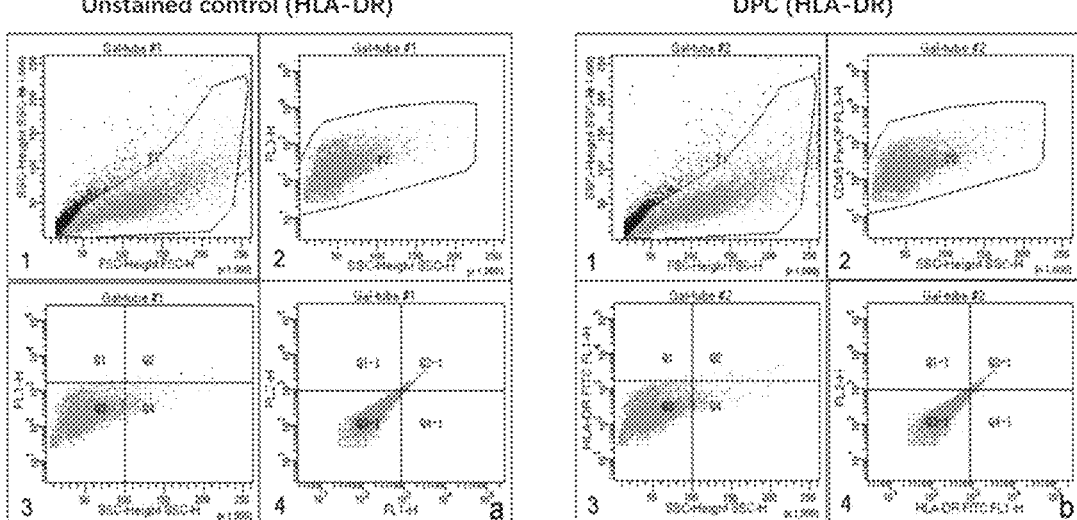
FIG. 7: Detection of HLA-DR antigens of neural stem cells induced by LY2157299 using flow cytometry.

4.2 Flow Cytometry Detection:

The HLA-DR antigens of neural stem cells induced by LY2157299 were detected by flow cytometry. HLA-DR is an MHC class II molecule whose expression is critical for the antigen-presenting function of cells and plays a key role in adoptive immune responses. The induced neural stem cells obtained in Example 2 were digested with EDTA, washed with DPBS, centrifuged to remove the supernatant, and $10^6$ Cells were resuspended in 100 μL of diluted primary antibody (CD45 PerCP, Abcam, Cat. No. ab157309; HLA-DR FITC, CST, Cat. No. 54126), incubated on ice for 1 hour in the dark, centrifuged to remove supernatant, and cells were resuspended in 500 μL of antibody dilution buffer (CST) and analyzed on a flow cytometer. Samples incubated without primary antibody were used as controls. The results are shown in FIG. 7, FIG. 7a is a negative control, FIG. 7b is the HLA-DR detection result of the neural stem cells obtained by LY2157299 induction. The result shows that the neural stem cells obtained by the LY inducing method do not express HLA-DR. This result is consistent with the result of Example 4.1.

Example 5: Effect of LY2157299 on Organoid Formation

Organoid culture was performed with human induced pluripotent stem cells. Organoid inducing medium was formulated as follows: NouvNeu basal medium supplemented with 12.5 μM LY21.57299. Induced pluripotent stem cells were digested to single cells by Accutase, seeded in 15-bottom-ultra-low attachment 96-well plates at a ratio of 9000 cells/150 mL of brain organoid inducing medium per well. 10 μM ROCK inhibitor Y-27632 (Selleck, 51049) was added, and the cells were placed in a 37° C., 5% carbon dioxide cell incubator for 24 hours (Panasonic, model: MCO-18AC). Y-27632-free fresh organoid inducing medium was changed the following day until day 10. Day 10 the organoids were transferred to ultra-low-attachment 6-well plates and the medium was changed to NouvNeu001 basal medium supplemented with 2% B27 cell culture additive. The culture was conducted at 37° C. in a 5% $CO_2$ cell culture incubator on a horizontal rotator at 80 rpm until day 120.

The control experiment was carried out according to the published method (Clair B et. al, Nat Methods. 2019, November; 16 (11): 1169-1175). N2B27 was used as the basic medium for organ like culture. The cerebral organoid inducing medium for control experiment was formulated as follows: The N2B27 basal medium was supplemented with 10 μM SB-431542, 100 nM LDN-193189 and 2 μM XAV-939. The rest of the operations are as above. The method is abbreviated as the N2B27 method in the invention and illustrations.

Figure 8:
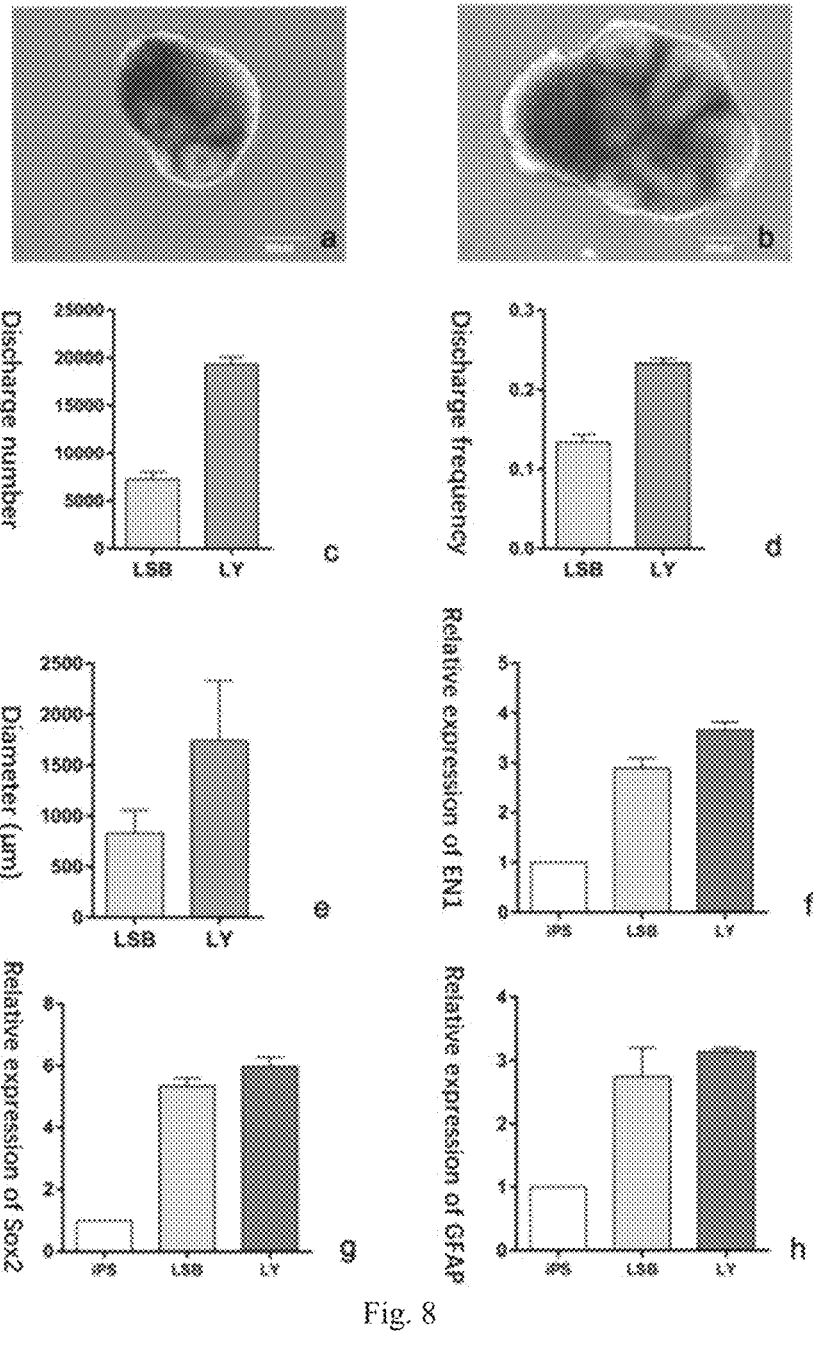
FIG. 8 LY2157299 can induce the generation of cerebral organoids.

Organoids were photographed by Leica Dmi8. The brain organoids were photographed and their diameters were measured. The results are shown in FIG. 8a, FIG. 8b, and FIG. 8e.

Induced brain organoids were subjected to the detection of spontaneous cell firing signals using multi-channel electrodes. Brain organoids induced for 120 days were digested with 10% trypsin/EDTA at 37° C. for 5-8 minutes. A 96-well MEA system multi-channel electrode plate (AXION Biosystem, US) was taken with 100 ng/mL poly-1-lysine (Sigma-Aldrich, P4707) for coating, placed in 37° C., 5% carbon dioxide cell incubator (Panasonic, model: MCO-18AC) for 12 hours. Take out the poly-1-lysine coating MEA multi-channel electrode plate, aspirated poly-1-lysine, washed with sterilized water 3 times, and used a PBS solution containing 3 ng/mL gelatin (Laminin, SIGMA ALDRICH, Cat. No.: 12020) as the nerve cell coating matrix, added to the MEA multi-channel electrode plate, placed in a 37° C., 5% carbon dioxide cell incubator for 3 hours, After the MEA multi-channel electrode plate was coated, the plate was seeded with digested organoid mix cells following the $5.0 \times 10^5$ cells per well. Place the seeded MEA multi-channel electrode plate in the MEA chamber, adjust the cell culture conditions in AxIS Navigator 2.0.2 software to 37° C., 5% carbon dioxide, and run for 10 minutes until the chamber environment is stable. Spontaneous cell firing signals were recorded with AxIS Navigator 2.0.2 software (AXION Biosystem, US), The experimental results showed that the neurons induced by the NouNeu system exhibited good electrophysiological activity. When a multichannel motor system was used to detect the cell spontaneous discharge, we can obtain the following conclusion by comparing the discharge number per cell unit time (FIG. 8C) and the average discharge rate (FIG. 8D): compared with the N2B27 control inducing method, the LY inducing method has more active electrophysiological activity.

Using Q-PCR to detect the transcriptional changes of different marker genes after the formation of brain organoids: The total RNA of brain organoids obtained by different methods for 120 days and the control of human induced pluripotent stem cells were respectively used Rneasy Mini or Micro Kit (QIAGEN) to extract. 1 mg of RNA was used to synthesize cDNA by using the SuperScript III First-Strand Synthesis System (Invitrogen). SYBR Premix Ex Tac) (TaKaRa) and Thermal Cycler Dice Real Time System (TaKaRa) were used for labeling and reaction of Quan-titative PCR, and Beta-actin was used as internal reference. All data were analyzed using the delta-Ct method. Three replicates were used for each group of experiments, and variance statistics were performed. The primer sequences used to identify the encoding genes for the different cell markers are shown in Table 5. Both brain organoids formed by LY-inducing method and N2B27 controlling group could produce glial cells, neural progenitors, and neurons (FIGS. 8f-8g).

TABLE 5

| Primers used for brain organoid detection Q-PCR | | |
|---|---|---|
| Gene | Primer sequences | SEQ ID NO. |
| EN1-F | GGACAATGACGTTGAAACGCAGCA | SEQ ID NO: 21 |
| EN1-R | AAGGTCGTAAGCGGTTTGGCTAGA | SEQ ID NO: 22 |
| SOX2-F | CATGCAGGTTGACACCGTTGG | SEQ ID NO: 1 |
| SOX2-R | ATGGATTCTCGGCAGACTGATTCA | SEQ ID NO: 2 |
| GFAP-F | CTGGAGAGGAAGATTGAGTCGC | SEQ ID NO: 23 |
| GFAP-R | ACGTCAAGCTCCACATGGACCT | SEQ ID NO: 24 |
| CASP3-F | GGAAGCGAATCAATGGACTCTGG | SEQ ID NO: 5 |
| CASP3-R | GCATCGACATCTGTACCAGACC | SEQ ID NO: 6 |
| ACTIN-F | TCCCTGGAGAAGAGCTACGA | SEQ ID NO: 9 |
| ACTIN-R | AGCACTGTGTTGGCGTACAG | SEQ ID NO: 10 |

Taken together, LY2157299 can induce the generation of cerebral organoids, which have electrophysiological functions and the expression of key genes. In addition, the cerebral organoids formed by the LY inducing method had a larger diameter and had more active electrophysiological functions compared to the N2B27 control inducing method.

All documents mentioned herein are incorporated by reference in their entirety in this application. In addition, it should be understood that after reading the above-mentioned teaching content of the present invention, those skilled in the art can make various changes or modifications to the present invention, and the modifications of these equivalent forms also fall within the scope defined by the claims of the present application.

What is claimed is:

1. An inducing medium for neural stem cells and organoids, wherein the inducing medium consists of basal medium and 10 nM-100 µM TGF-β inhibitor; the basal medium consists of Dulbecco's Modified Eagle/F12 Medium, 1% minimum essential medium non-essential amino acids, 0.5 g/L sodium chloride, 13.6 µg/L sodium selenite, 22 µg/mL insulin and 100 ng/mL recombinant human transferrin;

wherein the TGF-β inhibitor is 4-[2-(6-methylpyridin-2-yl)-5,6-dihydro-4H-pyrrolo[1,2-b]pyrazol-3-yl]quinoline-6-carboxamide.

2. The inducing medium of claim 1, wherein the concentration of the TGF-β inhibitor is 12.5 µM.

3. A method for inducing the formation of neural stem cells, wherein the inducing medium as claimed in claim 1 is used for adherent culture of pluripotent stem cells.

4. The method of claim 3, wherein the pluripotent stem cells are mammalian pluripotent stem cells.

5. The method of claim 4, wherein the pluripotent stem cells are human pluripotent stem cells.

6. The method of claim 5, wherein the adherent culture is performed in the presence of a basement membrane preparation.

7. The method of claim 6, wherein the basement membrane preparation is one or a combination of two or more of Matrigel, laminin, and vitronectin.

8. A method for further differentiation of neural stem cells into neuronal cells, wherein the neural stem cells are obtained by the method as claimed in claim 3, and inducing differentiation substances are added to the medium to culture until neurons form.

9. The method of claim 8, wherein the inducing differentiation substances are CHIR99021, SU5402, and DAPT, and the neural stem cells further differentiate into nociceptor neurons.

10. The method of claim 8, wherein the inducing differentiation substances are Purmorphamine and TGF-β3, and the neural stem cells further differentiate into dopaminergic neurons.

11. The method of claim 8, wherein the inducing differentiation substance is retinyl acetate, and the neural stem cells further differentiate into photoreceptor neurons.

12. A type of brain-like organs inducing medium, which is consisting of the neural stem cells inducing medium of claim 2 and an additive; wherein the additive is ROCK inhibitor Y-27632.

13. A method for inducing the formation of brain-like organs, wherein the pluripotent stem cells are cultured by using the brain-like organs inducing medium of claim 12; replace the medium of claim 12 with brain-like organs inducing medium without Y-27632 the next day, change the medium daily, and on the 10th day, replace it with the basal medium in claim 1, and add 2% B27 cell culture additive to cultivate until the 120th day.

\* \* \* \* \*